United States Patent [19]

Lafon

[11] Patent Number: 4,616,047

[45] Date of Patent: Oct. 7, 1986

[54] GALENIC FORM FOR ORAL ADMINISTRATION AND ITS METHOD OF PREPARATION BY LYOPHILIZATION OF AN OIL-IN-WATER EMULSION

[75] Inventor: Louis Lafon, Paris, France

[73] Assignee: Laboratoire L. Lafon, Alfort, France

[21] Appl. No.: 714,686

[22] Filed: Mar. 21, 1985

[30] Foreign Application Priority Data

Mar. 30, 1984 [FR] France ............................ 84 05058

[51] Int. Cl.$^4$ .............................................. A61K 9/50
[52] U.S. Cl. ........................................ 523/105; 34/5;
53/440; 424/22; 426/384; 426/385
[58] Field of Search ................... 34/5; 426/384, 385;
424/22; 53/440; 523/105

[56] References Cited

U.S. PATENT DOCUMENTS

| | | | |
|---|---|---|---|
| 2,520,939 | 9/1950 | Kowaleski et al. | 426/384 |
| 3,464,834 | 9/1969 | Laskin | 426/385 |
| 3,855,712 | 12/1974 | Blonde | 34/5 |
| 3,939,260 | 2/1976 | Lafon | 34/5 |
| 3,961,424 | 6/1976 | Elerath | 34/5 |
| 4,001,944 | 1/1977 | Williams | 34/5 |
| 4,146,971 | 4/1979 | Bornstein et al. | 34/5 |
| 4,273,762 | 6/1981 | McAleer et al. | 34/5 |
| 4,295,280 | 10/1981 | Krupey | 34/5 |
| 4,490,407 | 12/1984 | Lafon | 34/5 |
| 4,521,975 | 6/1985 | Bailey | 34/5 |

FOREIGN PATENT DOCUMENTS

| | | |
|---|---|---|
| 2017373 | 4/1971 | Fed. Rep. of Germany . |
| 806723 | 12/1958 | United Kingdom . |
| 1328641 | 8/1973 | United Kingdom . |

OTHER PUBLICATIONS

Chemical Abstracts, vol. 88, No. 6, Feb. 6, 1978, p. 254, No. 4169s (10-21-1977).
Chemical Abstracts, vol. 68, 1968, p. 9544, No. 98627m (1966).
Chemical Abstracts, vol. 87, No. 16, p. 323, No. 122707c (Oct. 1977).
Chemical Abstracts, vol. 91, No. 3, p. 497, No. 18602m, (Jul. 16, 1979).

*Primary Examiner*—Ronald W. Griffin
*Attorney, Agent, or Firm*—Garrettson Ellis; George H. Gerstman

[57] ABSTRACT

This invention is concerned with a method for preparing a novel porous galenic form by lyophilization of an oil-in-water emulsion containing at least one pharmaceutically active ingredient, which comprises the following steps:

(a) preparation of the lipid phase by stirring at a temperature lower than or equal to 80° C. so as to mix all the lipid-phase components, the lipid phase thus prepared being in the liquid state;

(b) preparation of the aqueous phase, which comprises at least one substance selected from the group consisting of organic fillers and thickening agents, by stirring at a temperature lower than or equal to 80° C. so as to mix the water and the other components of the aqueous phase;

(c) preparation of an emulsion under stirring at a temperature within the range of 10° C. to 80° C. by introducing the liquid lipid phase into the aqueous phase so as to ensure that the resulting emulsion is homogeneous;

(d) distribution of the resulting mixture into alveolar packs;

(e) freezing of the contents of the alveolar packs at a temperature within the range of −20° C. to −50° C. followed by lyophilization of said contents under a pressure within the range of approximately 80 Pa to approximately 0.13 Pa with a heat supply such that the temperature of the treated mass is always lower than the initial melting temperature of said mass;

the parmaceutically active substance being introduced prior to step (d), if necessary by fractions.

The invention also relates to the galenic form obtained in accordance with this method and constituting a novel industrial product.

23 Claims, 1 Drawing Figure

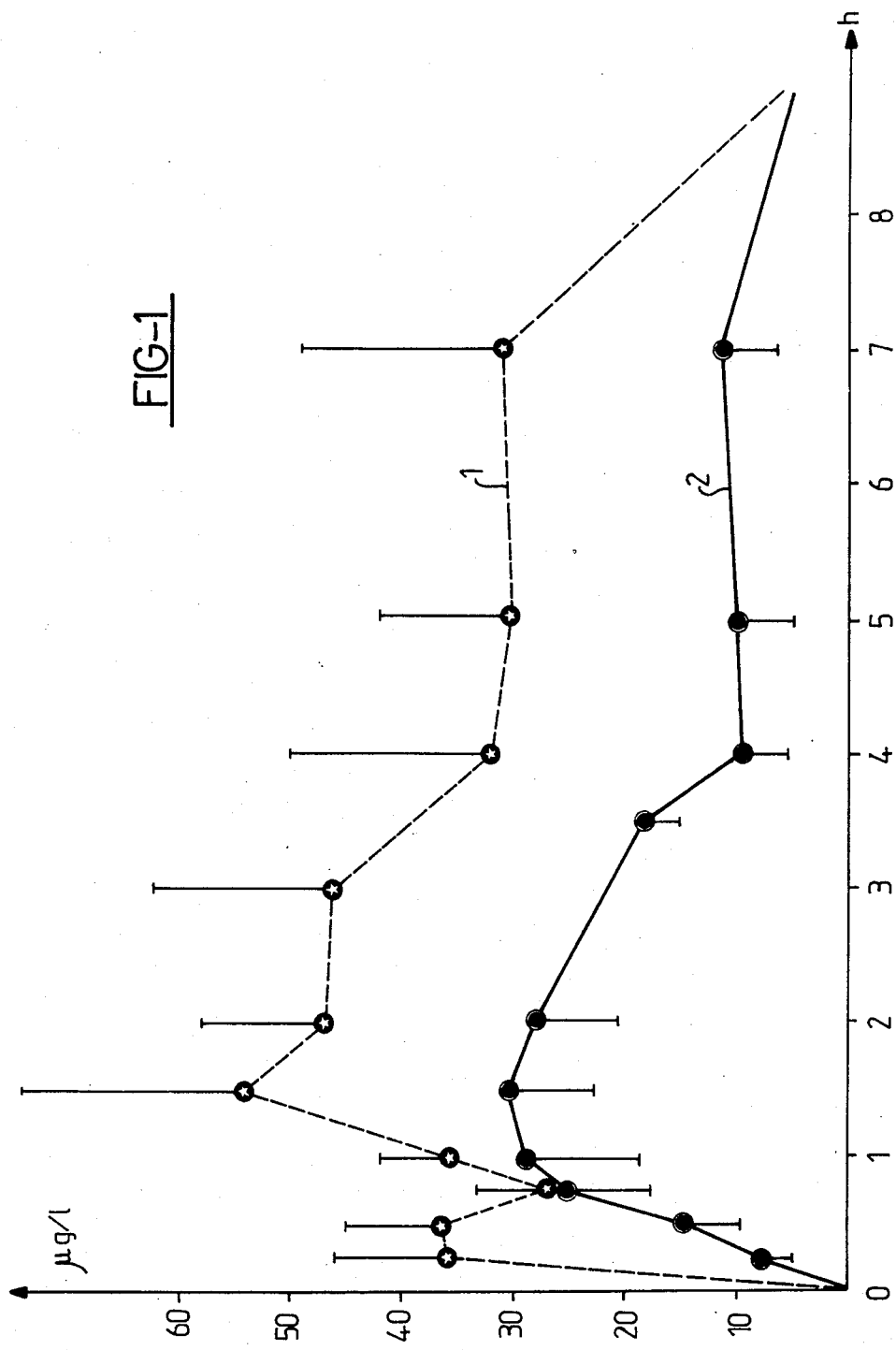

GALENIC FORM FOR ORAL ADMINISTRATION AND ITS METHOD OF PREPARATION BY LYOPHILIZATION OF AN OIL-IN-WATER EMULSION

The present invention relates to an industrial product consisting of a novel galenic form for oral administration of the solid oral emulsion type. The invention is mainly concerned with the method of preparation of this novel galenic form by lyophilization of an emulsion of the oil-in-water type.

It is known that emulsions constitute a liquid galenic form which is of interest in the biopharmaceutical field for oral administration. It is in fact possible in an emulsion system to introduce a wide range of substances, especially auxiliary substances such as fat-absorbent products, surface-active products, solubilizing agents, solvents, and so on, which provide a certain number of advantages, namely as follows:

modification of the absorption of medicinal drugs:
either in order to achieve enhanced bioavailability,
or to defer the release of active ingredients;
protection of the labile or fragile active ingredients which are liable to be degraded by an unfavorable pH medium or by enzymes of the digestive tract;
improvement by means of suitable adjuvants, in the tolerance of certain aggressive active ingredients (for example the anti-inflammatory agents and certain antibiotics) with respect to the mucous membranes of the digestive system.

However, this liquid galenic form is out of date since it gives rise in the first place to a certain number of technical problems:

it is limited to stable active ingredients, especially in the aqueous phase;
it is not applicable to associations of substances which are incompatible with each other in the aqueous phase;
for the preservation of an emulsion of this type, its formulation essentially requires the presence of a certain number of preserving agents which are not always conducive to tolerance;
the emulsions are heat-sensitive and entail the need for storage precautions.

In the second place, the practical utilization of the liquid galenic form is subject to a certain number of disadvantages arising from the presentation (a liquid packaged in a vial or bottle is not always convenient in ambulatory treatment), from the time limit allowed for use (once it has been opened, the vial must be used within a period of one to several weeks) and from the fact that dosing of the active ingredients is a random process, even when using dose spoons.

The present invention proposes a novel technical solution which involves lyophilization of an emulsion of the oil-in-water type in order to overcome the disadvantages of liquid emulsions while retaining their advantages.

The essential advantage of the solid emulsions in accordance with the invention over compressed tablets lies in the fact that the active ingredients are maintained in the state in which they are used in practice whereas, in the tablets, said active ingredients are liable to undergo extensive changes during the manufacturing process. For example, micronization which is often necessary for the purpose of improving the bioavailability of sparingly soluble products is attended by problems of wettability and reagglomeration by electrostatic phenomena. These phenomena are more marked in the case of the submicronic products which are obtained by various techniques such as nebulization, for example, and prove difficult and even impossible to recover by the usual methods. The present invention provides the only method for obtaining a solid form containing particles in such a finely divided state. In fact, in accordance with the invention, these disadvantages are overcome by utilizing a suspension which is perfectly dispersed and deflocculated by means of suitable adjuvants. As a result of lyophilization, this suspension is "frozen" and its properties are completely restored at the moment of utilization of the solid form in accordance with the invention. The manufacture of tablets does not make it possible to retain said properties either directly or indirectly by addition of correcting means since the quantities of water and/or adjuvants which it is possible to employ are rarely sufficient to produce a dispersion of particles throughout the entire mass. In addition, the manufacture of tablets entails the use of other adjuvants which are specific to this form (lubricants, for example) and are liable on the contrary to produce a flocculating or agglutinating effect.

Moreover, the compression itself produces by definition an agglomeration of the particles which, after disintegration, no longer redisperse in a unitary state. Even in the event of "flash disintegration", it proves difficult to maintain integrity of the initial particle-size distribution of a substance in tablet form. For various reasons (concealment of taste, protection, spread-out or delayed action), it is sometimes necessary to coat the particles of the active ingredient or to fix them on a support or vehicle of the resin type. The method in accordance with the invention makes it possible to maintain the integrity of the above-mentioned coating or fixation of particles which are too fragile in the majority of instances to withstand the mechanical effects of compression.

Finally, the mixtures to be compressed must have particular characteristics of "compressibility" which are usually conferred artificially. When the unitary dose is of high value and the active ingredient has poor characteristics of compressibility, it is difficult to produce flash-disintegration tablets since the granulation and binding agents which are necessary in order to improve these characteristics can only have the effect of retarding the rate of disintegration.

A further advantage of the lyophilized emulsion in accordance with the invention lies in both qualitative and quantitative broadening of the range of suitable adjuvants for achieving enhanced bioavailability and tolerance.

Thus it is possible in accordance with the invention to incorporate active ingredients provided in the form of fluid, soft, dry, waxy extracts of either animal or vegetable origin and if necessary agents for increasing bioavailability such as, for example, natural or synthetic phospholipids which are employed for the formation of liposomes, factors of passage and diffusion of medicinal substances (especially alphachymotrypsin, hyaluronidase, etc...) and/or products which are capable of reducing the viscosity of the active ingredients and of improving cell-capillary exchanges.

While the size and conditions of manufacture of the tablets and other galenic forms such as soft capsules or gelatine coated capsules able to contain lipid excipients and consequently active ingredients which are partially or totally soluble therein have the effect of limiting the quantity and nature of the adjuvants which can be employed for these galenic forms, the form in accordance with the invention is not subject to any of these restrictions since it can be made from a very wide variety of active ingredients irrespective of the value of their unitary dose. Finally, it should be pointed out that, in the case of utilization of fragile or highly reactive active ingredients, the granulation which is necessary for manufacture of the tablets is liable to produce changes or incompatibilities. Now it has been found that cold-state manufacture of the novel forms in accordance with the invention removes this drawback since the rate of any possible reactions and degradations is negligible at low temperatures.

It is also known that the following patent specifications: U.S. Pat. No. 4,178,695, GB-A-No. 1 227,744, GB-A-No. 1 310,824 and GB-A-No. 1 328,641 have already proposed methods of preparation of pharmaceutical, dietetic or cosmetic forms by lyophilization of at least one active ingredient in solution or suspension in water or an organic solvent or else in an emulsion of the oil-in-water type. The solution proposed in accordance with the invention is distinguished from the technical solutions of the prior art by the operating modes employed. By virtue of these operating modes, the end product is endowed with unexpected properties, especially in regard to preservation of the active ingredients and in regard to disintegration.

In accordance with the invention, the method for preparing a galenic form for oral administration by lyophilization of an oil-in-water emulsion containing at least one pharmaceutically active ingredient essentially comprises:

(a) preparing the lipid phase by stirring at a temperature lower than or equal to 80° C. so as to mix all the lipid-phase components, whereby said lipid phase is liquid, (b) preparing the aqueous phase, which comprises at least one substance selected from the group consisting of organic fillers and thickening agents, by stirring at a temperature lower than or equal to 80° C. so as to mix the water and the other components of said aqueous phase, (c) preparing an emulsion under stirring at a temperature within the range of 10° C. to 80° C. by introducing the liquid lipid phase into the aqueous phase in order to obtain a homogeneous emulsion, (d) distributing the resultant mixture into alveolar packs, (e) freezing the contents of said alveolar packs at a temperature within the range of −20° C. to −50° C., then lyophilizing said contents under a pressure within the approximate range of $6 \times 10^{-1}$ to $10^{-3}$ mmHg (that is, between approximately 80 and approximately 0.13 Pa) with a heat supply such that the temperature of the treated mass is always lower than the starting melting temperature of said mass, the pharmaceutically active substance being incorporated prior to step (d), that is to say either at the time of preparation of the lipid phase of step (a) or at the time of preparation of the aqueous phase of step (b) or in the homogeneous emulsion obtained in step (c) or else at low temperature (between −5° C. and −1° C.) after step (c) but prior to distribution in alveolar packs of step (d).

In this specification, the expression "pharmaceutically active substance" is understood to refer to any therapeutically effective ingredient or any association of at least two therapeutically effective ingredients in which said ingredients are either isolated (for example: an active ingredient present in the lipid phase and a second active ingredient present in the aqueous phase, or else an encapsulated or coated active ingredient and a second active ingredient present in either of the two phases) or else intimately mixed.

The essential lipid component contained in the lipid phase consists of at least one substance selected from the group comprising the $C_6$–$C_{20}$-fatty acids, the $C_6$–$C_{30}$-fatty alcohols, the derivatives of said fatty acids, the derivatives of said fatty alcohols, the fats of animal, vegetable and synthetic origin and mixtures of the thereof. Among the fatty acid derivatives which are suitable for use in accordance with the invention, special mention can be made of the esters and in particular (1) the triglycerides of ($C_8$–$C_{18}$) fatty acids obtained from the caprylic, capric, myristic, oleic, linoleic, stearic acids and their mixtures (especially the triglycerides of the acids of the $C_8$–$C_{10}$ fraction extracted from coconut oil), and (2) the glycerides of saturated ($C_{12}$–$C_{18}$-)fatty acids (which are polyoxyethylenated). Among the fatty alcohol derivatives can be mentioned in particular the esters. Worthy of note among the fats of animal, vegetable and synthetic origin are the oils and the waxes such as, in particular, hydrogenated castor oil, cotton oil, sesame oil, soybean oil, peanut oil, halibut oil, beeswax, the ketowaxes (condensates of alkylene oxides—ethylene and/or propylene oxides—with saturated fatty alcohols) and their mixtures.

If necessary, the lipid phase can contain in addition one or several surface-active agents (preferably non-ionic surfactants) and/or one or several essences.

In practical terms, if no account is taken of the weight of pharmaceutically active substance or of a fraction of this latter to be incorporated if necessary in step (a), the essential component as defined in the foregoing can represent approximately 60 to 100% by weight with respect to the weight of the lipid phase. Nevertheless, there are cases in which said essential component can represent quantities which are distinctly smaller than 60% by weight with respect to the weight of said lipid phase.

The aqueous phase which constitutes the continuous phase of the emulsion to be prepared in accordance with the invention comprises an essential component, namely a substance selected from the group of organic fillers, thickening agents and their mixtures.

In practice, it is not easy to make a distinction between organic fillers and thickening agents inasmuch as it is possible in general to find substances which may belong to both categories. For the sake of simplicity, the term "organic fillers" is used in this specification to designate essentially water-soluble substances having a relatively low molecular weight and the term "thickening agents" is used to designate substances which are water-soluble, water-dispersible or capable of being readily dispersed in water and having binding properties or swelling properties in water as well as a higher molecular weight than the organic fillers.

The organic fillers which are suited for use in accordance with the invention include in particular lactose, whole milk powder, semi-skimmed milk powder, skimmed milk powder, glycocoll, mannitol, the maltodextrins and their mixtures. Suitable thickening agents which are worthy of mention include the polysaccharides such as in particular the natural gums (gum arabic, gum tragacanth, etc.) and the synthetic gums (glycosylglucans in accordance with U.S. Pat. Nos. 3,507,290 and 3,659,015), the cellulose derivatives, the pectins, the bentonites, the colloidal silicas, polyvinyl alcohol (PVA), polyvinylpyrrolidone (PVP), the acrylic polymers and copolymers, and the mixtures thereof.

In practice, if no account is taken of the weight of the pharmaceutically active substance or a fraction of said active substance to be incorporated if necessary in step (b), the group comprising organic filler and thickening means represents approximately 10 to 85% by weight and advantageously 15 to 65% by weight with respect to the weight of the aqueous phase of step (b).

The group comprising organic filler and thickening means takes part in the formation of the matrix. In broad terms, it may be stated that the organic filler forms the matrix proper and the thickening agent cooperates in the achievement of cohesion and dimensional stability of the matrix. Moreover, the group comprising organic filler and thickening agent performs a contributory function in the adsorption of volatile substances and in the formation of the porous structure of the end product and consequently plays an important part in the release of the pharmaceutically active substance. It is also possible to improve the bioavailability by employing microgranules of active ingredients coated with a thin gastroresistant envelope.

Among the dispersing means which can be incorporated in the aqueous phase in step (b) or in the lipid phase in step (a), recourse can be had to known substances which are suitable for this purpose in the galenic field. Particularly suitable are the non-ionic, anionic and cationic surface-active agents. Thus in step (b), it is possible to incorporate one or several surface-active agents selected from the following:

the non-ionic surface-active agents such as the polyoxyethylenated polysorbates or esters of sorbitan (marketed under the trade name of "Tween"), the sorbitan esters (marketed under the trade name of "Span"), the copolymers of ethylene oxide and of propylene oxide, the fatty polyethoxyethers of glycerides (especially polyethoxylated castor oil), the cetyl ethers of polyoxyethyleneglycol, the palmitostearates of polyoxyethyleneglycol, the soybean and egg lecithins and the like;

the anionic surface-active agents such as in particular the ($C_4$–$C_{12}$)-dialkyl-sulfosuccinates, especially sodium dioctylsulfosuccinate;

the cationic surface-active agents such as in particular the quaternary ammonium compounds.

As indicated earlier, these surface-active agents can also be introduced in step (a) at the time of preparation of the lipid phase, particularly in the case of the non-ionic surface-active agents.

In summary, while it is possible to employ one or a number of surface-active agents in each of the lipid and aqueous phases, it is essential in accordance with the invention to ensure that at least one of these two phases contains a surface-active agent. Advantageously, if no account is taken of the weight of the pharmaceutically active substance or of that fraction of this latter which is to be incorporated in step (a) and/or in step (b), the quantity of surface-active agent to be employed represents approximately 0.2% to 10% by weight and preferably 0.4% to 8% by weight with respect to the total weight of the lipid and aqueous phases.

Other substances which may be employed in step (b) include (1) the natural or synthetic sweetening agents such as saccharose, glucose, xylose, sorbitol, saccharin, the saccharinates (especially the sodium, potassium and calcium saccharinates), the cyclamates (especially the sodium, potassium and calcium cyclamates), aspartame, and (2) taste-modifying agents (in particular for the purpose of concealing the bitter after-taste of synthetic sweeteners of the saccharinate or cyclamate type) such as in particular the citric, ascorbic and tartaric acids, and aromas.

If so required, it is also possible to incorporate amino-acids in the aqueous phase of step (b).

The quantity of water employed in step (b) is not critical. Generally speaking, this quantity is limited to the amount which is strictly necessary in order to dissolve and/or disperse the components of the aqueous phase, to produce the emulsion of step (c) and to limit the power consumption costs required for carrying out step (e). It will readily be understood that, if the ingredients employed in step (b) are liquid substances, the water content may be considerably reduced. The water to be employed is a purified water and especially distilled, bidistilled or demineralized water.

The emulsion of step (c) is produced in accordance with the invention by stirring at a temperature within the range of 10° C. to 80° C. by pouring the liquid lipidic phase into the aqueous phase. This operation is advantageously performed at a temperature within the range of 15° C. to 60° C. Although it has proved necessary to heat the lipid and aqueous phases in steps (a) and (b), it may be found advantageous to allow said phases to cool before pouring the lipid phase which is still in the liquid state into the aqueous phase. In practice, the two phases are in accordance with the invention at the same temperature when one phase is poured into the other. Nevertheless, it may be useful in certain particular instances to provide a temperature gradient by pouring the lipid phase into the aqueous phase at a lipid-phase temperature which is lower than that of said aqueous phase.

In a preferred mode of execution of the invention, the emulsion of step (c) is prepared in such a manner as to ensure that the weight of the pharmaceutically active substance which may be present is not taken into account and that the weight ratio of lipid phase to aqueous phase is within the range of 1:100 to 1:4 and preferably within the range of 1:50 to 1:6.

Advantageously, the duration of step (e) is at least eight hours. The freezing time (which depends on the desired temperature within the range of −20° C. to −50° C.) is at least one hour on an average in order to obtain by means of a plate-type industrial freezer an identical internal temperature of each of the masses which are distributed within the alveolar packs. The drying time is at least seven hours, taking into account the fact that provision is made in accordance with the invention for a progressive heat supply.

In a preferred embodiment of the method in accordance with the invention, the very fine state of the globules of the emulsion obtained in step (c) is maintained intact by means of the following recommended procedure: (1) the homogeneous emulsion obtained in step (c) is cooled by stirring to a temperature below 0° C. but preferably within the range of −1° C. to −5° C. and better still within the range of −2° C. to −4° C. by introducing it into a scraped-surface exchanger in order to obtain a frozen emulsion;

(2) the frozen emulsion thus obtained is distributed in alveolar packs in step (d);

(3) the freezing and drying operation is then performed in accordance with step (e), the total freezing and drying time being at least eight hours.

As indicated in the foregoing, the pharmaceutically active substance is introduced if necessary in fractions from step (a) until initiation of step (d). If an active ingredient is sensitive to water, it is introduced into the lipid phase during step (a). If there are two active ingredients which are liable to be incompatible with each other prior to administration, they are incorporated separately, one in the lipid phase and the other in the aqueous phase. Advantageously, the incorporation of one of the active ingredients constituting the pharmaceutically active mass is recommended after step (c) prior to commencement of step (d). As will readily be understood, the pharmaceutically active substance can be introduced in fractions in step (a), in step (b), in step (c) and/or prior to commencement of step (d) after execution of step (c).

In the case of active ingredients which are particularly sensitive in particular to heat, it is recommended in accordance with a preferred embodiment or mode of application of the invention to introduce said ingredients in a pre-cooled state into the aforementioned frozen emulsion while stirring at a temperature below 0° C. but preferably within the range of −1° C. to −5° C. and better still within the range of −2° C. to −4° C., then to distribute the resultant mixture within alveolar packs and then to carry out freezing and drying.

It will of course be apparent that, if necessary, the operations involving introduction of the pharmaceutically active substance and described in the foregoing can be carried out with one or a number of active ingredients in the form of coated granules.

The galenic form obtained in accordance with the invention is porous, lightweight and stable while retaining its initial geometry. The geometrical shape is defined by the mold or so-called alveolar pack in which the product has been distributed. Thus the geometrical shape can be hemispherical, ovoid, cubic, parallelepipedal, conical, frusto-conical, pyramidal, cylindrical, and so on.

The results of tests which have been undertaken show that the method in accordance with the invention retains the initial properties or the properties developed during preparation of the pharmaceutically active substance, prevents phenomena of recrystallization and polymorphism, prevents denaturation of the fragile active ingredients, and offers the further advantage of stabilizing the partition coefficient of the active ingredients of the pharmaceutically active substance between the dispersed oily phase and the continuous aqueous phase, which is liable to vary in particular when there is a variation in parameters such as temperature.

The galenic form in accordance with the invention can be administered with or without water. It can be taken by placing it under the tongue, crunching between the teeth or allowing it to disintegrate in the mouth. A liquid emulsion can also be obtained extemporaneously by dispersing it in water.

Other advantages and features of the invention will be more apparent from a perusal of the following examples of preparation which are given solely by way of explanatory illustration and not in any limiting sense.

EXAMPLE 1

Tiadenol at 1200 mg

Unitary formula:

| | | | |
|---|---|---|---|
| A | Tiadenol | 1200 | mg |
| B | Triglyceride of caprylic and capric acids | 200 | mg |
| | Polysorbate 60 | 20 | mg |
| | Polyethoxyether of fatty glycerides | 20 | mg |
| C | Sodium saccharinate | 10 | mg |
| | Dextran 70 000 | 50 | mg |
| | Lactose | 300 | mg |
| | Demineralized water | 1400 | mg |

Manufacturing technique:

1. Mix and heat the ingredients of the lipid phase B at 65° C.

2. Dissolve and disperse the elements of the aqueous phase C and heat said phase to 65° C.

3. Pour B into C while stirring, continue the stirring operation and allow to cool to 45° C.

4. Add the active ingredient A to the emulsion B+C at 45° C. and homogenize by means of a rapid disperser in order to obtain a fine and stable emulsion.

5. Distribute the emulsion thus obtained into alveolar packs in a proportion of 3.20±0.05 g per alveolar pack.

6. The alveolar packs are driven to low temperature on the plates of a lyophilizer. Allow the temperature to attain equilibrium at −35° C. over a period of one hour and begin the lyophilization process by production of a vacuum within the vessel (approximately $10^{-1}$ mmHg, namely approximately 13.3 Pa) and by heating the plates on which the alveolar packs are placed. The drying process takes place progressively with a supply of heat such that the temperature of the mass is necessarily maintained below its starting melting point. The length of the freezing-drying cycle is approximately 10 to 12 hours.

In accordance with this technique, the fragments thus obtained have a uniform shape, a porous state, a unitary weight of 1800±50 mg and each containing approximately 1200 mg of tiadenol. These alveolar packs containing said fragments are heat-sealed with sheets of aluminum/PVC complex and packaged.

EXAMPLE 2

Erythromycin at 1000 mg

| | | | |
|---|---|---|---|
| A | Erythromycin ethylsuccinate (in a sufficient quantity for 1000 mg of base) | 1175 | mg |
| B | Triglyceride of caprylic, capric and linoleic acids | 250 | mg |
| | Soybean lecithin | 20 | mg |
| C | Copolymer of polyoxyethylene, of polyoxypropylene and of propyleneglycol | 60 | mg |
| | Sodium saccharinate | 10 | mg |
| | Hydroxypropylmethylcellulose | 10 | mg |
| | Powdered, semi-skimmed milk | 300 | mg |
| | Ammonium glycyrrhizinate | 5 | mg |
| | Bidistilled water | 2000 | mg |

The process is performed as in Example 1 by introducing the active ingredient A into the emulsion B+C at a temperature below 20° C. and by distributing into each alveolar pack 3.83±0.05 g of the resultant emulsion.

EXAMPLE 3

Glafenin at 200 mg

| | | | |
|---|---|---|---|
| A | Glafenin | 200 mg | |
| B | Hydrogenated and stripped ($C_8$-$C_{12}$) coconut oil | 50 mg | |
| | Soybean lecithin | 10 mg | |
| C | Sodium dioctylsulfosuccinate | 10 mg | |
| | Sodium saccharinate | 5 mg | |
| | Aspartame | 20 mg | |
| | Powdered whole milk | 150 mg | |
| | Mannitol | 500 mg | |
| | Demineralized water | 1000 mg | |

The process is performed as in Example 1 by introducing the active ingredient A at 15°-20° C. in the emulsion B+C and by distributing within each alveolar pack 1.945+0.050 g of the resultant emulsion.

EXAMPLE 4

Glafenin at 150 mg

| | | |
|---|---|---|
| A | Glafenin | 150 mg |
| B | Polyoxyethylenated oleic glycerides | 50 mg |
| | Sorbitan monostearate | 10 mg |
| | Polyoxyethylene monostearate | 10 mg |
| C | Saccharin | 10 mg |
| | Lactose | 500 mg |
| | Saccharose monopalmitate | 1 mg |
| | Distilled water | 1000 mg |

The process is performed as in Example 3.

EXAMPLE 5

Floctafenin at 200 mg

| | | |
|---|---|---|
| A | Floctafenin | 200 mg |
| B | Hydrogenated castor oil | 100 mg |
| | Polysorbate 60 | 10 mg |
| | Sorbitan monooleate | 10 mg |
| C | Sodium saccharinate | 10 mg |
| | Hydroxypropylmethylcellulose | 5 mg |
| | Mannitol | 500 mg |
| | Demineralized water | 1000 mg |

Preparation at 60° C. for each phase B and C and addition of A to B+C at 60° C., followed by treatment in accordance with the process described in Example 1.

EXAMPLE 6

Micronized spironolactone at 50 mg

| | | |
|---|---|---|
| A | Micronized spironolactone | 50 mg |
| B | Triglycerides of capric and caprylic acids | 25 mg |
| | Soybean lecithin | 5 mg |
| C | Saccharose monopalmitate | 0.5 mg |
| | Powdered whole milk | 100 mg |
| | Lactose | 300 mg |
| | Purified water | 700 mg |

The process is performed as in Example 1 by introducing A in the emulsion B+C at 20° C.

EXAMPLE 7

Indometacin at 75 mg

| | | |
|---|---|---|
| A | Indometacin | 75 mg |
| B | Polyoxyethylenated oleolinoleic glycerides | 50 mg |
| | Polyoxyethylene(2)cetyl ether | 10 g |
| | Polyoxyethylene(10)cetyl ether | 10 mg |
| C | Saccharose distearate | 5 mg |
| | Powdered whole milk | 100 mg |
| | Lactose | 300 mg |
| | Distilled water | 700 mg |

The process is performed as in Example 1 in order to prepare the emulsion B+C. This emulsion is then introduced into a scraped-surface exchanger and cooled. When the temperature attained −2° C., the active ingredient A which has previously been cooled to −2° C. is introduced and stirring is continued in order to obtain a homogeneous "frozen emulsion". The cold emulsion is distributed in alveolar packs, whereupon freezing and drying are carried out as in Example 1.

EXAMPLE 8

Naproxene at 250 mg

| | | |
|---|---|---|
| A | Naproxene | 250 mg |
| | Olive oil | 80 mg |
| | Polysorbate 60 | 15 mg |
| | Sorbitan monostearate | 15 mg |
| C | Glycyrrhizine | 7 mg |
| | Aspartame | 15 mg |
| | Mannitol | 500 mg |
| | Distilled water | 1200 mg |
| D | Coconut aroma | 50 mg |
| | Anise aroma | 5 mg |

The process is performed as in Example 1 by preparing the phases B and C at 65° C. and by introducing A and D in the emulsion B+C at 40° C.

EXAMPLE 9

Vitamin complex

| | | |
|---|---|---|
| A | Vitamin A palmitate | 2.3 mg |
| | D,L-α-tocopherol acetate | 10 mg |
| | Calciferol (D3) | 0.4 mg |
| | Polysorbate 80 | 20 mg |
| | Mandarin oil | 20 mg |
| B | Thiamine mononitrate | 2 mg |
| | Riboflavin | 2 mg |
| | Calcium pantothenate | 9.3 mg |
| | Pyridoxine hydrochloride | 1 mg |
| | Nicotinamide | 15 mg |
| | Ginseng (extract) | 40 mg |
| | Saccharose | 25 mg |
| | Polymer of ethylene oxide Propylene oxide and propyleneglycol | 50 mg |
| | Sodium saccharinate | 13 mg |
| | Lactose | 700 mg |
| | Demineralized water | 1000 mg |
| C | Ascorbic acid coated with ethylcellulose | 60 mg |

1. Dissolve the mixture A.
2. Disperse the mixture B.
3. Mix A with B while stirring, and homogenize. 4. Pass the emulsion obtained in a scraped-surface exchanger and cool to a temperature of approximately −2° C. to −3° C., add C, then homogenize.
5. Proceed as indicated in Example 7 for distribution in alveolar packs, freezing and drying.

EXAMPLE 10

Buflomedil hydrochloride at 150 mg

| | | |
|---|---|---|
| A | Buflomedil hydrochloride | 150 mg |
|   | Cation - exchange resin | 170 mg |
| B | Triglyceride of caprylic and capric acids | 50 mg |
|   | Polysorbate 60 | 5 mg |
|   | Polyethoxyether of fatty glycerides | 5 mg |
| C | Sodium saccharinate | 15 mg |
|   | Aspartame | 15 mg |
|   | Dextran 70 000 | 40 mg |
|   | Mannitol | 527 mg |
|   | Orange oil | 16 mg |
|   | Aluminum and magnesium silicate | 7 mg |
|   | Demineralized water | 1000 mg |

The process is performed as in the foregoing Example 7. A kinetic study on dogs clearly points to the fact that the product obtained in accordance with Example 10 effectively releases in vivo the buflomedil hydrochloride adsorbed on the cation-exchange resin.

COMPARATIVE TESTS

The summary given below describes part of the comparative tests which have been carried out with the novel oral forms in accordance with the invention.

TEST I

For the purpose of comparison, the product obtained in accordance with the foregoing Example 1 containing 1200 mg of tiadenol and the commercial specialty known as "Fonlipol" (three tablets each containing 400 mg of tiadenol) were administered clinically to patients suffering from hyperlipemia (group of eight male adults per product to be tested by oral administration, each patient receiving the same dose (1200 mg) of tiadenol. It is recalled that tiadenol, which has the following developed formula:

$$HOCH_2CH_2S(CH_2)_{10}SCH_2CH_2OH$$

and corresponds to the systematic nomenclature of 1,10-bis(2-hydroxyethylthio)decane, is a reference lipid reducing agent described in particular in DE-A-No. 2,038,836.

There were then determined the serum concentrations of tiadenol (mg/l) as a function of time (hr). The results have been recorded in FIG. 1, in which curve 1 relating to the product of Example 1 has been plotted from minimum values of the confidence interval and in which curve 2 relating to the compressed tablet form previously known has been plotted from maximum values of the confidence interval.

A comparison of curves 1 and 2 reveals the fact that the latency period after administration of the product of Example 1 is considerably reduced with respect to the tablets. There is also observed a statistically significant difference in regard to the concentrations of tiadenol in the blood by comparing the areas beneath the concentration/time curves.

TEST II

For the purpose of comparison, an identical dose (150 mg) of buflomedil hydrochloride was administered orally to dogs (distributed in batches of nine animals per batch). From the galenic standpoint, this active ingredient was packaged in three different forms:

one batch of animals received the product of Example 10 above (A);

one batch of animals received the compressed tablet of buflomedil hydrochloride which is marketed under the trade name of "Fonzylane" (Registered trademark) (cf. in particular Dictionnaire Vidal, O. V.P., Paris 1983, page 525) (B); and one batch of animals received a tablet in which the active ingredient was associated with 170 mg of the same cation-exchange resin considered in Example 10 (C).

It has been found that the adsorption resin contained in the product of Example 10 does not prevent the release of the active ingredient in vivo. A kinetic study of bioavailability in vivo shows that the areas beneath the curve of plasmatic concentrations/time are not different in the case of groups A and B and that there exists a statistically significant difference in the case of batches A and B with respect to batch C since batch C gives plasmatic concentrations which are lower than those of batches and B over the test period considered.

What is claimed is:

1. A method for preparing a galenic form for oral administration by lyophilization of an oil-in-water emulsion containing at least one pharmaceutically active ingredient and obtained from a lipid phase and an aqueous phase, wherein said method comprises:

(a) preparing the lipid phase by stirring at a temperature
   lower than or equal to 80° C. so as to mix all the lipid-phase components, whereby said lipid phase is liquid, (b) preparing the aqueous phase, by stirring at a temperature lower than or equal to 80° C. so as to mix the water and the other components of said aqueous phase, said aqueous phase including an organic filler selected from the group consisting of lactose, whole milk powder, semi-skimmed milk powder, skimmed milk powder, glycocoll, mannitol, maltodextrins, and mixtures thereof; said aqueous phase also containing a thickening agent selected from the group consisting of natural natural and synthetic gums, cellulose derivatives, pectins, bentonites, colloidal silicas, polyvinyl alcohol, polyvinylpyrrolidone, acrylic polymers and copolymers, and mixtures thereof, said organic filler and thickening agent constituting from 10 to 85% by weight of the total aqueous phase, not counting the pharmaceutically active substance present;

(c) preparing an emulsion under stirring at a temperature within the range of 10° C. to 80° C. by introducing the liquid lipid phase into the aqueous phase in order to obtain a homogeneous emulsion, (d) distributing the resulting mixture into alveolar packs, (e) freezing the contents of said alveolar packs at a temperature within the range of −20° C. to −50° C., then lyophilizing said contents under a pressure within the approximate range of 80 Pa to 0.13 Pa, with a heat supply such that the temperature of the treated mass is always lower than the starting melting temperature of said mass, the pharmaceutically effective material being incorporated before step (d).

2. A method according to claim 1, wherein the pharmaceutically active substance is incorporated from step (a) up to the point of commencement of step (d), if necessary by fractions.

3. A method according to claim 1, wherein at least a fraction of the pharmaceutically active substance is incorporated in step (c).

4. A method according to claim 1, wherein at least a fraction of the pharmaceutically active substance is incorporated at a temperature below 0° C. in the homogeneous emulsion resulting from step (c).

5. The method of claim 4 in which said temperature is −1° C. to −5° C.

6. A method according to claim 1, wherein a surface-active agent is introduced in at least one of steps (a) and (b).

7. A method according to claim 6 wherein, if the weight of the pharmaceutically active substance present in steps (a) and (b) is not taken into account, the surface-active agent represents approximately 0.2% to 10% by weight with respect to the total weight of the lipid and aqueous phases.

8. The method of claim 7 in which the amount of surface-active agent present is from 0.4 to 8% by weight with respect to the total weight of lipid and aqueous phases, disregarding pharmaceutically active substance present.

9. A method according to claim 1 wherein, if the weight of the pharmaceutically active substance present in step (b) is not taken into account, the group consisting of organic filler and thickening agent represents approximately 10 to 85% by weight with respect to the weight of the aqueous phase.

10. The method of claim 9 in which said organic filler and thickening agent represent 15 to 65% of weight of said aqueous phase, disregarding the amount of pharmaceutically active substance present.

11. A method according to claim 1 wherein, if the weight of the pharmaceutically active substance present in steps (a) and (b) is not taken into account, the emulsion of step (c) is prepared in such a manner as to ensure that the weight ratio of lipid phase to aqueous phase is within the range of 1:100 to 1:4.

12. The method of claim 11 in which the weight ratio of lipid phase to aqueous phase is within the range of 1:50 to 1:6.

13. A method according to claim 1, wherein the duration of step (e) is at least eight hours, the freezing time at a temperature within the range of −20° C. to −50° C. being at least one hour on an average, a progressive heat supply being provided during the drying process.

14. A method according to claim 1 wherein, after step (c), the homogeneous emulsion obtained in said step (c) is cooled by stirring to a temperature below 0° C. in order to obtain a frozen emulsion which is then subjected to steps (d) and (e).

15. The method of claim 14 in which said temperature is −1° to −5° C.

16. A porous galenic form, which is obtained by means of the method according to claim 1.

17. A method for preparing a galenic form for oral administration by lyophilization of an oil-in-water emulsion containing at least one pharmaceutically active ingredient and obtained from a lipid phase and an aqueous phase, wherein said method comprises:

(a) preparing the lipid phase by stirring at a temperature lower than or equal to 80° C. so as to mix all the lipid-phase components, whereby said lipid phase is liquid, (b) preparing the aqueous phase by stirring at a temperature lower than or equal to 80° C. so as to mix the water and the other components of said aqueous phase, said aqueous phase containing milk powder as an organic filler and a thickening agent selected from the group consisting of natural and synthetic gums, cellulose derivatives, pectins, bentonites, collidal silicas, polyvinyl alcohol polyvinylpyrrolidone, acrylic polymers and copolymers, and mixtures thereof, said organic filler and thickening agent representing about 10 to 85% by weight of the aqueous phase, not counting the weight of said pharmaceutically active ingredient present;

(c) preparing an emulsion under stirring at a temperature within the range of 10° C. to 80° C. by introducing the liquid phase into the aqueous phase in order to obtain a homogeneous emulsion, the weight ratio of lipid phase to aqueous phase being within the range of 1:100 to 1:4, and the temperature of said lipid and aqueous phases on mixing being substantially equal;

(d) distributing the resulting mixture into alveolar packs, (e) freezing the contents of said alveolar packs at a temperature within −20° to −50° C., and then lyophilizing said contents under a pressure within the approximate range of 80 Pa to 0.13 Pa, with a heat supply such that the temperature of the treated mass is always lower than the starting melting temperature of said mass, the pharmaceutically effective material being incorporated before step (d).

18. The method of claim 17 in which at least a fraction of the pharmaceutically active ingredient is incorporated at a temperature brlow 0° C. in the homogeneous emulsion resulting from step (c).

19. The method according to claim 18 wherein a surface active agent is introduced in at least one of steps (a) and (b).

20. The method of claim 19 in which from 0.2 to 10% by weight of said surface active agent is present, based on the total weight of the lipid and aqueous phases without counting pharmaceutically active ingredient present.

21. The method of claim 20 wherein the duration of step (e) is at least 8 hours, the freezing time at a temperature within the range of −20° C. to −50° C. being at least one hour, a progressive heat supply being provided during said step to accelerate lyophilization.

22. The method of claim 21 in which the amount of organic filler and thickening agent present in said aqueous phase prior to lyophilization is 15 to 65% by weight, and the weight ratio of the lipid phase to the aqueous phase is from 1:50 to 1:6, disregarding the weight of pharmaceutically active ingredient present.

23. A porous, galenic form, for the oral administration of pharmaceuticals, obtained by the method of claim 17.

* * * * *